United States Patent [19]

Lin

[11] Patent Number: 4,831,159

[45] Date of Patent: May 16, 1989

[54] PROCESS FOR HYDROFORMYLATION OF N-VINYL-2-PYRROLIDINONE

[75] Inventor: Jiang-Jen Lin, Round Rock, Tex.

[73] Assignee: Texaco Inc., White Plains, N.Y.

[21] Appl. No.: 876,495

[22] Filed: Jun. 20, 1986

[51] Int. Cl.$^4$ .......................................... C07P 207/263
[52] U.S. Cl. .................................................. 548/551
[58] Field of Search .......................... 548/551; 568/454

[56] References Cited

U.S. PATENT DOCUMENTS 3,636,034  1/1972  Ohsumi et al. ...................... 568/451

FOREIGN PATENT DOCUMENTS 0096986  12/1983  United Kingdom ................ 568/454

OTHER PUBLICATIONS

J. Falbe, "New Syntheses with Carbon Monoxide", Springer–Verlag, Berlin (1980), pp. 128 & 129.
Cotton et al., "Advanced Inorganic Chemistry", 3rd Ed., Interscience (1972), pp. 790–793.
Stille, J. Org. Chem. (1980) 45, pp. 2145–2151.

*Primary Examiner*—David B. Springer
*Attorney, Agent, or Firm*—Jack H. Park; Kenneth R. Priem; Cynthia L. Kendrick

[57] ABSTRACT

A process is disclosed for preparing isomeric aldehydes by contacting N-vinyl-2-pyrrolidinone and synthesis gas in the presence of a rhodium-containing compound with or without additional phosphine ligand and a solvent. The alpha and beta isomeric aldehydes such as 2-N-(2-pyrrolionyl)propanaldehyde and 3-N-(2-pyrrolidonyl)propanaldehyde can be converted to 1,2- or 1,3-diaminopropanes via reductive amination or to alcohol amines via reduction.

1 Claim, No Drawings

PROCESS FOR HYDROFORMYLATION OF N-VINYL-2-PYRROLIDINONE

FIELD OF THE INVENTION

This invention relates to a process for the preparation of isomeric aldehydes from N-vinyl-2-pyrrolidinone and synthesis gas in the presence of a rhodium-containing compound and a solvent.

More specifically, this invention concerns the hydroformylation of N-vinyl-2-pyrrolidinone to products such as 2-N-(2-pyrrolidonyl)propanaldehyde and 3-N-(2-pyrrolidonyl)propanaldehyde using a rhodium catalyst at a low pressure with or without additional phosphine ligand and the reductive amination of these compounds to the corresponding diaminopropanes and hydroxyaminopropanes. The products can also undergo oxidation to form amino acids.

BACKGROUND OF THE INVENTION

A very good overview of hydroformylation is found in *Adv. Organometallic Chemistry* 17 (1979) "Hydroformylation", by Pruett. The reaction mechanism is discussed as well as substrates, products and by-products, catalysts other than cobalt and rhodium, etc.

N-vinyl-2-pyrrolidinone is a commercially available intermediate compound usually formed by the reaction of 2-pyrrolidinone and acetylene. It is useful as a monomer for various copolymerizations. It does not appear the concept of hydroformylating N-vinyl-2-pyrrolidinone to produce isomeric products has been accomplished using low pressures.

In *Journal of Orangometallic Chemistry*, 268 (1984) 167–174, the hydrocarbonylation and hydroformylation of β-substituted N-vinylphthalimides catalyzed by Rh or Pd catalysts has been reported. N-protected aminoacid derivatives were prepared. The reaction is strongly affected by the nature of the substitutents. The required substrates were prepared by a relatively complex scheme involving alkylation of phthalamide and Ru-catalyzed isomerization.

In *J. Org. Chem.* 1980, 45, 2145–2151, Stille discusses the asymmetric hydroformylation and hydroxycarboxylation of enamides. Here it was stated that previously rhodium-catalyzed asymmetric hydroformylation has been confined to simple olefins and it was found that much higher optical yields were obtained with rhodium catalyzed asymmetric hydrogenation of vinyl amides as opposed to the use of simple olefins. In this study, enamides included N-vinylsuccinimide, N-vinylphthalamide, N-acyl-2-pyrrolines, N-vinylacetamide, N-allylacetamide. The structures of these compounds affected the reaction rate and selectivity. It was reported that trisubstituted enamides, N-(2-methylpropenyl)acetamide and N-(2-methylpropenyl) phthalimide were completely unreactive and linear disubstituted enamides reacted sluggishly in comparison with cyclic enamides. The reaction of N-vinyl-pyrrolidinone, a cyclic monoamido olefin, was not included.

The hydroformylation of N-acylated aminoolefins is demonstrated in J. Falbe, "New Synthesis with Carbon Monoxide", Springer-Verlag, Berlin, Heidelberg, New York, 1980. At page 129 data shows the hydroformylation of N-vinylpyrrolidone using $Rh_2O_3$+phenothiazine as a catalyst. However, here the pressure used is 700 bars or approximately 10,150 psig.

The comparison of Rh and Co catalyst on product selectivities (linear vs. branched products) was also revealed in Falbe, "New Synthesis With Carbon Monoxide", P. 128.

Starting from N-vinylphthalimide, a 78% yield of the 3-phthalimidopropanaldehyde and 2-phthalimidopropanaldehyde in a ratio of 2.5:1 was obtained. The Rh-related catalyst afforded a relatively reverse selectivity.

A study reported by Jardine in Polyhedron, No. 7-8, 569–605, 1982 provides insight into a comparison of carbonylhydrido tris(triphenylphosphine)rhodium(I), $RhH(CO)(PPh_3)_3$ as a hydroformylation catalyst compared with other reactions and concludes that, though $RhH(CO)(PPh_3)_3$ is the best hydroformylation catalyst, it is disappointing in other reactions. For instance, chlorotris(triphenylphosphine)rhodium(I) is probably a more generally useful hydrogenation catalyst and dichloro tris(triphenylphosphine)ruthenium(II) is probably a more effective isotope exchange catalyst.

Brown discusses reactivity and selectivity in catalysis by rhodium complexes in "Metals in Organic Synthesis" in *Chemistry and Industry*, 2 Oct. 1982. It was concluded that organorhodium complexes are uniquely effective in catalysis involving a series of linked intermediates where hydrogen, an olefin and possibly carbon monoxide are simultaneously coordinated and undergo intracomplex rearrangements. This article also discussed work involving asymmetric homogeneous hydrogenation where effective catalysts are chiral chelating biphosphines possessing a relatively rigid backbone and are asymmetric either at phosphorous or in the interphosphine chain. Further, a model for the mechanism of asymmetric hydrogenation is discussed. Vinyl acetates are mentioned as providing "good optical yields". Brown asserts there is much potential in organic synthesis for a reaction which effects catalytic conversion of terminal or other α-olefins into homologous aldehydes with high and controllable regioselectivity. The selectivity is thought to be dependent on reaction variables and concentration of free triphenylphosphine.

In an article entitled "Synthesis of Intermediates by Rhodium-Catalyzed Hydroformylation" in *Angew. Chem. Ind. Ed. Engl.* 19, 178–183 (1980), Himmele et al. discuss asymmetric hydroformylations in the presence of chiral phosphanes, but state that the enantiometric purity of the products is not high enough for industrial-scale synthesis (For example 20–30%).

These references do not appear to discuss the synthesis of amino-propanaldehydes, diaminopropanes and hydroxyaminopropanes by the reaction of commercially available N-vinyl-2-pyrrolidinone with syngas in the presence of a rhodium-containing compound at a low pressure with or without additional phosphine ligand and mild temperature and the subsequent reductive amination of the aldehydes to the final products. Diaminopropanes can be used in medicinals, dyes, rubber accelerators and analytical reagents. Diaminopropanes such as 1,2-diaminopropane can also be used in the production of epoxy resins. The final product distribution is controlled by regioselectivity of N-vinyl-2-pyrrolidinone hydroformylation.

SUMMARY OF THE INVENTION

In accordance with the present invention N-vinyl-2-pyrrolidinone and synthesis gas undergo hydroformylation in the presence of a rhodium-containing compound and a solvent at a temperature of 70°–150° C. and a pressure of 500–1000 psi. These products are converted to amino-propanaldehydes, diaminopropanes and hydroxyaminopropanes by reductive amination or to alcohol amines via reduction. The conversion of N-vinyl-2-pyrrolidinone reaches as high as 95% and the selectivity for alpha-aldehydes reaches as high as 85%.

DETAILED DESCRIPTION OF THE PREFERRED INVENTION

In the narrower and more preferred practice of this invention isomeric aldehydes are prepared from N-vinyl-2-pyrrolidinone and synthesis gas by a process which comprises contacting said pyrrolidinone and synthesis gas with a catalyst system comprising a rhodium-containing compound with a phosphine ligand and a solvent at a temperature of at least 50° C. and a pressure of at least 500 psi until there is substantial formation of the desired aldehydes and subsequent conversion to diamino products via reductive amination.

The general reaction can be represented by:

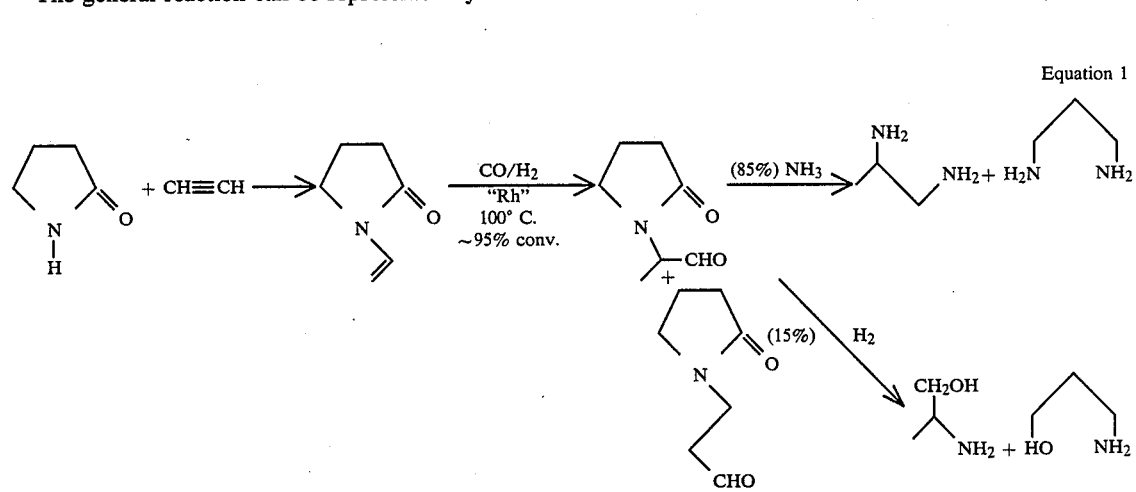

Equation 1

Recovery of the isomeric aldehydes and by-products from the reaction product can be carried out in any convenient or conventional manner such as by distillation, extraction etc.

In general, the components of the hydroformylation reaction mixture, including the N-vinyl-2-pyrrolidinone compound, rhodium-containing compound and solvent may be added in any sequence as long as good agitation is employed to provide a good dispersion or a homogeneous reaction mixture. For example, the following represent some variations insofar as the addition of catalyst components, solvent and alkyl acrylate addition that can be made without departing from the inventive process. These modifications include:

1. The catalyst may be preformed and added to the solvent prior to addition of the N-vinyl-2-pyrrolidinone and other reactants.

2. Preferably, to minimize stability problems with the catalyst, the catalyst is best formed in situ, usually by mixing the solvent and N-vinyl-2-pyrrolidinone followed by the addition of the rhodium-containing compound and phosphorous-containing compound to form the reaction mixture.

3. After using either variation 1 or 2 the catalyst containing reaction mixture is pressurized with CO and hydrogen and heated until the product is formed.

The reactant used in the process of the invention comprises N-vinyl-2-pyrrolidinone. Alternatively the N-vinyl-2-pyrrolidinone can be prepared from 2-pyrrolidinone and acetylene.

The rhodium-containing compound to be used in the catalyst in practice of this invention may be chosen from a wide variety of organic or inorganic compounds, complexes, etc. as will be shown and illustrated below. It is only necessary that the catalyst precursor actually employed contain said rhodium in any of its ionic states. The actual catalytically active species is then believed to comprise rhodium in complex combination with one or more phosphine promoters and a solvent.

The rhodium compound can be selected from the group consisting of rhodium oxides, salts of inorganic acids, such as rhodium chloride, bromide, iodide, sulfide and salts of aliphatic monocarboxylic acids such as rhodium acetate, propionate, oxylate and malonate.

Other suitable inorganic or organic salt-like compounds falling within the scope of the invention are salts of heteropolyacids containing rhodium, such as the salts of alkalai metals or alkaline earth metals, ammonium salts or amine salts. Also useful are oxides of rhodium. By way of specific examples there may be mentioned as oxides: $Rh_2O$, $Rh_2O_3$, $RhO_2$ and $RhO_3$.

Salts of inorganic acids include rhodium chloride $RhCl_3$, rhodium bromide $RhBr_3$, rhodium iodide $RhI_3$, and rhodium sulfide $Rh_2S_3$. Salts of carboxylic acids include rhodium acetate $[Rh(CH_3CO_2)_3]$ and rhodium oxylate $[Rh_2(C_2O_4)_3]$.

Other derivatives which can be employed to carry out the process of the invention include the carbonyl derivatives of rhodium such as rhodium tricarbonyl $[Rh(CO)_3]$, rhodium tetracarbonyl $[Rh(CO)_4]_2$, the compound $Rh_4(CO)_{17}$ and the halogencarbonyl derivatives of rhodium such as rhodium dicarbonyl chloride $[Rh(CO)_2Cl]_2$, rhodium dicarbonyl bromide $[Rh(CO)_2]Br$ and rhodium dicarbonyl iodide $[Rh(CO)_2]I$.

The preferred catalyst is a rhodium carbonyl containing a large excess of a tertiary phosphine such as triphenylphosphine. The best example is hydridorhodium tris(triphenylphosphine)rhodium.

In the first embodiment of the process of this invention N-vinyl-2-pyrrolidinone is reacted with carbon monoxide and hydrogen in the presence of a hydroformylation catalyst comprising $HRh(CO)(PPh_3)_3$, excess triphenylphosphine and a solvent to form alpha and beta isomeric aldehydes. These isomeric aldehydes will include 2-N-(2-pyrrolidonyl)propanaldehyde and 3-N-

(2-pyrrolidonyl)propanaldehyde. The reaction can be represented by the equation:

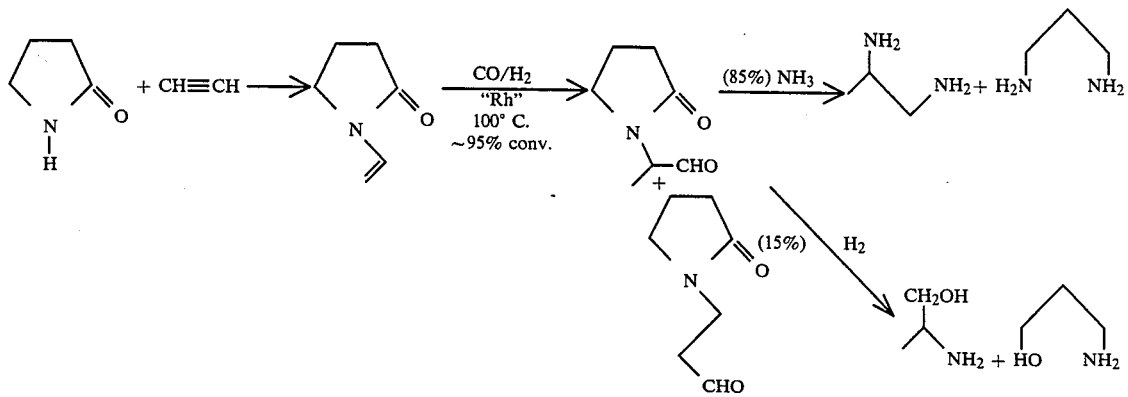

Equation 1

The reaction allows up to greater than 95% conversion of N-vinyl-2-pyrrolidinone and up to 85% selectivity for the alpha-aldehydes. In order to obtain such favorable results an excess of triphenylphosphine ligand appears to be essential.

In the second step of the invention the reductive amination of the isomeric aldehydes afforded the aminopropanaldehydes, diaminopropanes and hyroxyaminopropanes.

The temperature range which can be employed for hydroformylation is a variable which is dependent upon experimental factors including the particular pyrrolidinone compound employed, the total pressure, the mole ratio of hydrogen and carbon monoxide used, the concentrations of reactants and catalyst, and particularly the choice of rhodium catalyst and solvent among other things. Using N-vinyl-2-pyrrolidinone or 2-pyrrolidinone and acetylene as the substrate and HRh(CO)(PPh$_3$)$_3$ as a representative catalyst, an operable range is from about 70° C. to 150° C. or more when superatmospheric pressures of greater than 100 psig are employed. A narrower range of 80° C. to 150° C. represents the preferred temperature range when the aforementioned pyrrolidinones are hydroformylated.

The pressure range which can be employed for hydroformylation is a variable which is also dependent on the factors mentioned above. Using HRh(CO)(PPh$_3$)$_3$ and p-dioxane as a representative catalyst and solvent, and N-vinyl-2-pyrrolidinone as the substrate, an operable pressure range is from about 500 to 4000 psig, or more with the mole ratio of H$_2$:CO being 1:1 when a temperature range of from about 70° to 150° C. is employed. A narrower range of from 500 to 2000 psig represents the preferred pressure range when the narrower temperature range of 80° C. to 120° C. is employed The H$_2$:CO mole ratio may be varied over a range of from 30:1 to 1:30 when suitable temperatures and pressures are employed. A preferred narrower range is from 2:1 to 1:2 of hydrogen:carbon monoxide.

As previously indicated in the analogous discussion on temperatures and pressures required in the reaction, experimental variables are important in arriving at reaction times. Generally, substantial conversions (up to 95%) of the N-vinyl-2-pyrrolidinone to isomeric aldehydes can almost always be accomplished within 18 hours, with 2 to 4 hours representing the more usual reaction time interval.

In the process of this invention the molar ratio of rhodium-containing compound to the triphosphine ligand is significant. The experimental work performed indicates that an excess of ligand of about at least 3 moles of triphenylphosphine for each mole of rhodium-compound complex is required for good selectivity. Preferably a ratio of from 1 to 500 moles of triphenylphosphine for each mole of rhodium-containing compound has been established to yield the optimum amount of formate product. Most preferred is ca. 50 moles per mole of rhodium compound. This preferred ratio is based upon the hydroformylation of N-vinyl-2-pyrrolidinone.

Experimental work indicates that an initial molar ratio of 100 moles to 1000 moles of N-vinyl-2-pyrrolidinone per mole of rhodium catalyst can be employed in most instances. The minimal ratio would be about $10^{-3}$ moles of catalyst per mole of pyrrolidinone.

The novel hydroformylation is run most conveniently in the presence of a solvent. The solvent useful in the process of this invention is an oxygenated hydrocarbon, i.e., a compound composed only of carbon, hydrogen and oxygen and one in which the only oxygen atoms present are in ether groups, ester groups, ketone carbonyl groups or hydroxyl groups of alcohols. Generally, the oxygenated hydrocarbon will contain 3 to 12 carbon atoms and preferably a maximum of 3 oxygen atoms. The solvent must be substantially inert under reaction conditions.

Preferred ester type solvents are the aliphatic and acrylic carboxylic acid monoesters as exemplified by butyl acetate, methyl benzoate, isopropyl iso-butyrate, and propyl propionate as well as dimethyl adipate and dimethylphthalate. Useful alcohol-type solvents include monohydric alcohols such as cyclohexanol, 1-hexanol, 2-hexanol, neopentanol, 2-octanol, etc. Suitable ketone-type solvents include, for example, cyclic ketones such as cyclohexanone, 2-methylcyclohexanone, as well as acyclic ketones such as 2-pentanone, butanone, acetophenone, etc. Ethers which may be utilized as solvents include cyclic, acyclic and heterocyclic materials. Preferred ethers are the heterocyclic ethers as illustrated by 1,4-dioxane and 1,3-dioxane. Other suitable ether solvents include isopropyl propyl ether, diethylene glycol dibutyl ether, dibutyl ether, ethyl butyl ether, diphenyl ether, heptyl phenyl ether, anisole, tetrahydrofuran, etc., alkanols such as methanol and acid esters such as methyl acetate.

The most preferred solvents and those which seem to most noticeably effect an increase in selectivity to alpha-aldehydes include p-dioxane or toluene.

Hydroformylation products, including 2-N-(2-pyrrolidonyl)propanaldehyde and 3-N-(2-pyrrolidonyl)propanaldehyde may be isolated by the usual chemical or physical techniques, such as distillation, solvent extraction, chromatography, etc. Identification is by nuclear magnetic resonance. Unless otherwise specified all percentages are by weight and all temperatures are in centigrade rather than fahrenheit.

Conversion as defined herein represents the extent of conversion of the reacting pyrrolidinone to other products. Conversion is expressed as a percentile and is calculated by dividing the amount of N-vinyl-2-pyrrolidinone consumed during hydroformylation by the amount of acrylate originally charged and multiplying the quotient by 100.

Yield, as defined herein, represents the efficiency in catalyzing the desired hydroformylation reaction relative to other undesired reactions. In this instance hydroformylation to isomeric aldehydes is the desired conversion. Yield is expressed as a percentile, and is calculated by determining the amount of, for example, 2-N-(2-pyrrolidonyl)propanaldehyde and 3-N-(2-pyrrolidonyl)propanaldehyde product formed, divided by the amount of charged and multiplying the quotient obtained by 100.

Selectivity, as defined herein, is the efficiency in catalyzing a desired reaction relative to the other undesired conversion. Selectivity is expressed as a percentile, and is calculated by determining the amount of alpha or beta isomeric aldehyde formed, divided by the total amount of isomeric aldehydes formed, and multiplying the quotient obtained by 100.

Having described the inventive process in general terms, the following examples are submitted to supply specific and illustrative embodiments.

EXAMPLE I

A 300 ml magnedrive autoclave was charged with hydridocarbonyl tris(triphenylphosphine)rhodium(I) (0.046 g, 0.05 mmole), N-vinyl-2-pyrrolidinone (5.6 g, 0.05 mole) and p-dioxane (15.0). The reactor was purged of air with a mixture of $CO/H_2 = 1:1$. The initial pressure of 100 psi ($CO/H_2 = 1:1$) was added to the reactor and the system was heated to 120° C. Then the pressure was raised to 800 psi with a $CO/H_2$ mixture (1:1 molar ratio). The syngas pressure uptake was noted and 800 psi pressure was maintained by adding the $CO/H_2$ mixture through a gas tank. The reaction was held for four hours, then cooled to room temperature. The excess gas was vented and 19.7 g of homogeneous solution was obtained (greenish black solution).

The glc and H-nmr analyses showed the results of >95% N-vinyl-2-pyrrolidinone conversion, 85% selectivity to alpha-aldehyde and 15% selectivity to beta-aldehyde.

EXAMPLES II–V

In Examples II through V the same procedure was used as in Example I. No phosphine ligand was used in Example IV and different solvents were used in Examples III–V. The results of these experiments are shown in Table I.

It is noted that the product selectivities can be controlled by varying reaction temperature, solvent and ligand addition. The maximum selectivity to branched product at 85% (Example I) and selectivity to linear product at ~50% (Example V) were achieved. Therefore, the distribution of final products are adjustable.

TABLE I

Hydroformylation of N—vinyl-2-pyrrolidinone

| Examples | Catalyst[1] | Ligand | Substrate[2] | Solvent | Conditions[3] | Conv. % | alpha- | beta-isomer | Notes[4] |
|---|---|---|---|---|---|---|---|---|---|
| II | 0.046 g | 1.3 g | 5.6 g | 15.0 g p-dioxane | 100° C., 4 hr. | 80 | 66 | 33 | 20 g |
| III | 0.092 g | 1.3 g | 11.2 g | dimethylphthalate 30 g | 70° C., 4 hr. | 5 | — | — | 40.3 g |
|  |  |  |  |  |  | 95 | 65 | 35 | 41.2 g |
| IV | 0.092 g | None | 11.2 g | Toluene 30 g | 120° C., 2 hr. | 90 | 65 | 35 | — |
|  |  |  |  |  | 120° C., 4 hr. | 95 | 65 | 35 | 41.2 g |
| V | 0.092 g | 1.3 g | 11.2 g | Toluene 30 g | 90° C., 2 hr. | 40 | 48 | 52 | — |
|  |  |  |  |  | 90° C., 4 hr. | 66 | 55 | 44 | 42.5 g |

[1]Catalyst: Hydridocarbonyl tris-(triphenylphosphine)rhodium(I)
[2]Substrate: N—vinyl-2-pyrrolidinone
[3]Conditions: $CO/H_2 = 1:1$ molar ratio, 800 psi
[4]Product recovered weight

What is claimed is:

1. In the rhodium catalyzed hydroformylation of N-vinyl-2-pyrrolidone to produce predominantly linear aldehyde the improvement consisting essentially of using as the catalyst $RhHCO(PPh_3)_3$ with excess $PPh_3$ and a solvent at a temperature of 70° C. to 120° C. and a presuure of 600 psig to 1000 psig.

* * * * *